United States Patent [19]

Cates

[11] Patent Number: 4,591,582

[45] Date of Patent: May 27, 1986

[54] ORGANOPHOSPHORUS COMPOUNDS USEFUL AS ANTICONVULSANT AGENTS

[75] Inventor: Lindley A. Cates, Houston, Tex.

[73] Assignee: Research Corporation, New York, N.Y.

[21] Appl. No.: 601,149

[22] Filed: Apr. 17, 1984

[51] Int. Cl.[4] .............................................. A61K 31/66
[52] U.S. Cl. .................................................... 514/114
[58] Field of Search ........................................ 514/114

[56] References Cited
PUBLICATIONS

J.A.C.S., (1955), 77, 920.

*Primary Examiner*—Stanley J. Friedman
*Attorney, Agent, or Firm*—Scully, Scott, Murphy & Presser

[57] ABSTRACT

Organophosphorus compounds useful as anticonvulsant agents having the general formula:

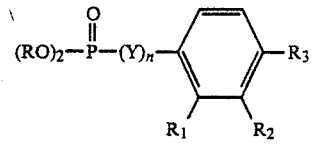

wherein R is alkyl, X is O or S, Y is O or S, n is an integer from 0 to 1, $R_1$, $R_2$ and $R_3$ are selected from the group consisting of $NH_2$ and

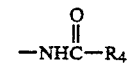

wherein $R_4$ is alkyl, with the proviso that only one of $R_1$, $R_2$ and $R_3$ can be $NH_2$ or

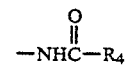

with the proviso that when n is 1, $R_1$ or $R_2$ or $R_3$ is

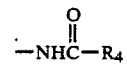

and with the further proviso that R is alkyl other than ethyl when $R_2$ is $-NH_2$.

11 Claims, 2 Drawing Figures

ORGANOPHOSPHORUS COMPOUNDS USEFUL AS ANTICONVULSANT AGENTS

BACKGROUND OF THE INVENTION

The work leading to this invention was sponsored in part by NIH Grant No. NS15704. The U.S. Government is granted a non-exclusive, royalty-free license.

This invention relates to novel organophosphorus compounds and more particularly to novel organophosphorus compounds useful as anticonvulsant agents.

Epilepsy refers to any of various disorders marked by disturbed electrical rhythms of the central nervous system and is typically manifested by convulsive attacks or seizures.

The prevalence of epilepsy is between 3 and 6 per 1,000 of the population. In the great majority of cases, the cause of the disease is unknown and the disease is referred to as "primary" or "idiopathic" epilepsy. When the cause is known the disease is referred to as "secondary" or "symptomatic" epilepsy. The treatment of the disease is approached essentially in the same manner for both primary and secondary epilepsy since the common object of treatment is the prevention of irreversible damage to neurons.

The therapeutic goal for treating epilepsy is to prevent seizures. If managed well with known antiepileptic drugs, approximately 75% of treated patients may have their seizures controlled in frequency. This means that there are essentially no known drugs available to adequately treat 25% of the patients who have epilepsy. The need, therefore, exists for new antiepileptic agents.

Epileptic seizures are convulsive activities. Since it is the seizures or convulsions that are attempted to be controlled by therapeutic treatment, antiepileptic drugs may also be termed anticonvulsant drugs. The terms antiepileptic and anticonvulsive are therefore intended to be interchangeable for the purposes of the description of the present invention.

Of the known anticonvulsant or antiepileptic drugs the major clinically useful drugs are phenytoin, phenobarbital, ethoxysuximide, and valproate. As discussed above, these drugs are generally only effective on approximately 75% of epileptic patients. Additionally, these drugs are known to exhibit adverse side effects due to varying degrees of toxicity.

It is also known that gamma-aminobutyric acid (GABA) serves as a major inhibitory neurotransmitter in the central nervous system (CNS) and is involved in several disease conditions as well as the action of some CNS depressant drugs. Since GABA does not penetrate the blood-brain barrier there have been investigations into agents which gain access to the CNS and then either mimic its activity or inhibit its metabolism with an accompanying increase in the concentration of GABA. See, for example, Saelens and Vinick: Agents affecting GABA in the CNS in "Annual Reports in Medicinal Chemistry", F. H. Clarke, Ed., Academic Press, New York, 1978, pp. 31–40. Increasing GABAergic transmission has been shown to be of benefit in certain convulsive disorders, e.g. epilepsy and Huntington's disease. See, Marsden, C. D.: GABA in relation to extrapyramidal disease, with particular relevance to animal models. In Krogsgaard-Larsen, P. Scheel-Kruger, J., and Kofard, H. (eds.): "GABA-Neurotransmitters." New York: Academic Press, 1979, pp. 295–307. This was successfully accomplished when highly hydrophilic GABA, with a calculated log P (octanol-water) value of −2.13, and its amide were incorporated into more lipophilic molecules. See, Kaplan et al.: New Anticonvulsants; Schiff bases of gamma-aminobutyric acid and gamma-aminobutyramide. J. Med. Chem. 23, 702–704, 1980. The log P values of these carrier compounds more closely approximate the 2.0±0.7 which has been determined to be optimum for CNS-acting drugs to penetrate into the CNS—(Lien et al., J. Pharm. Sci., 1973, 62, 246). Compounds resembling the activity of gamma-aminobutyric acid are therefore desirable anticonvulsant candidates.

SUMMARY OF THE INVENTION

Accordingly, it is one object of the present invention to provide new anticonvulsant agents.

It is another object of this inventon to provide anticonvulsant agents which are even more effective than previously known anticonvulsant drugs.

Still another object of the present invention is to provide anticonvulsant compounds which are less toxic than previously known anticonvulsant agents.

A still further object of this invention is to provide methods for treating convulsive disorders, including, inter alia, epilepsy, parkinsonism, Huntington's disease, cerebral palsy and the like.

These and other objects are accomplished herein by providing organophosphorus compounds useful as anticonvulsant agents having the general formula:

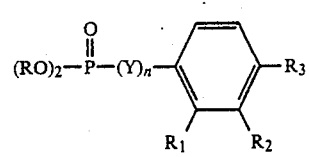

wherein R is alkyl, X is O or S, Y is O or S, n is an integer from 0 to 1, $R_1$, $R_2$ and $R_3$ are selected from the group consisting of $NH_2$ and

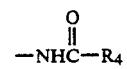

wherein $R_4$ is alkyl with the proviso that only one of $R_1$, $R_2$ and $R_3$ can be $NH_2$ or

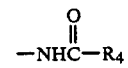

and with the further proviso that when n=1, $R_1$ or $R_2$ or $R_3$ is

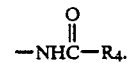

DETAILED DESCRIPTION OF THE INVENTION

Figure 1:
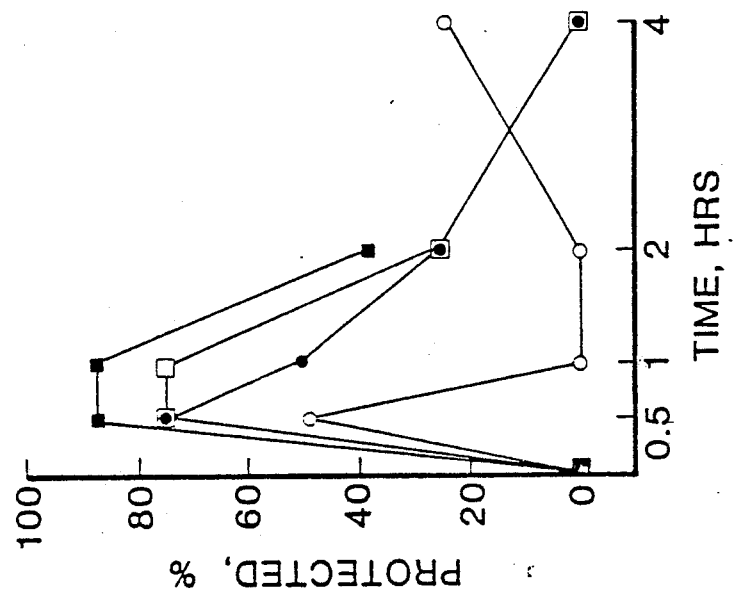
FIG. 1 is a graphical representation showing the time course of percent protection by intraperitoneally administered I–IV against seizures induced by maximal electroshock (MES) or subcutaneous pentylenetetrazol (Metrazol) (scMet). Key: (■) I (dimethyl ester of 3-aminophenylphosphonic acid) 400 mg/kg, scMet: (●) II (diethyl ester of 3-aminophenylphosphonic acid) 200 mg/kg, MES; (□) III (diisopropyl ester of 3-aminophenylphosphonic acid) 300 mg/kg, MES: (○) IV (diethyl-2-acetamidophenylphosphate) 300 mg/kg, MES.

In accordance with the present invention, it has been discovered that a certain class of organophosphorus compounds are excellent anticonvulsant agents. More particularly, these organophosphorus compounds have the general formula:

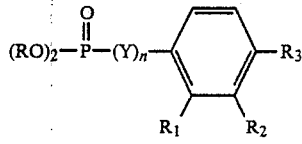

wherein

R is alkyl, X is O or S, Y is O or S, n is an integer from 0 to 1, $R_1$, $R_2$ and $R_3$ are selected from the groups consisting of $NH_2$ and

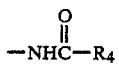

wherein $R_4$ is alkyl with the proviso that only one of $R_1$, $R_2$ and $R_3$ can be $NH_2$ or

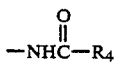

and with the further proviso that when n=1, $R_1$ or $R_2$ or $R_3$ is

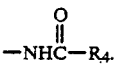

R is generally alkyl from 1 to 10 carbon atoms, such as methyl, propyl, isopropyl, pentyl, nonyl etc. $R_4$ is preferably alkyl from 1 to 6 carbon atoms.

Representative compounds within the above general formula found to be active anticonvulsants within the scope of the present invention include, for example, the dimethyl, diethyl and diisopropyl esters of 3-aminophenylphosphonic acid, diethyl-2-acetamidophenylphosphate and the like. Pharmaceutically acceptable non-toxic salts of the active compounds of this invention are also contemplated herein. Typical salts include maleates, citrates, HCl and the like. A preferred compound within the scope of the present invention is the dimethyl ester of 3-aminophenylphosphonic acid. This compound is found to be about 2.5 times better than valproic acid against maximal electroshock, an important determinant of protective effect. It is also 1.8 and 1.3 times better against two chemically induced seizures. Moreover, this compound has a superior neurotoxicity dose level.

Except for the diethyl ester of 3-aminophenylphosphonic acid, the organophosphorus compounds within the above formula are believed to be novel. The diethyl ester compound is disclosed in J. Am. Chem. Soc., 1955, 77, 920. No anticonvulsant activity is however suggested by this reference.

The novel organophosphorus compounds of the present invention can be prepared, for example, in the case of the amino compounds, by reducing (e.g. by hydrogenation in the presence of palladium, the respective dialkyl ester of nitrophenylphosphonic(thio)acid. The amido compounds are typically prepared by treatment of a hydroxyacylated-aniline with a phosphoro(thio)-chloridate in the presence of triethylamine or other HCl-scavenger.

The anticonvulsant agents of the present invention are found to be active in mammals e.g. animals and humans, when administered in amounts ranging from about 2 mg to about 300 mg per kilogram of body weight. The particular dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the intraarterial, intravenous, intramuscular, oral or subcutaneous routes.

The active compounds may be orally administered, for example, with an insert diluent or with an assimilable edible carrier, or they may be enclosed in hard or soft shell gelatin capsules, or they may be compressed into tablet, or they may be incorporated directly with the food of the diet. For oral therapeutic administration, the active compounds may be incorporated with excipients and used in the form of ingestible tablets, buccal tablets, troches, capsules, elixiers, suspensions, syrups, wafers, and the like. The amount of active compound in such therapeutically useful compositions is such that a suitable anticonvulsant dosage will be obtained.

The tablets, troches, pills, capsules, time release capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compounds may also be administered parenterally or intraperitoneally. Solutions of the active compound or pharmacologically acceptable salt can be prepared in water suitably mixed with a surfactant, if desired, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The present preferred methods of administration are oral and parenteral.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, pharmaceutically acceptable carrier includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are characteristics of the active material and the particular therapeutic effect to be achieved, and (b) the limitations inherent in the art of compounding such an active material for the treatment of disease in living subjects having a diseased condition in which bodily health is impaired as herein disclosed in detail.

In accordance with the present invention the amount of active ingredients administered is a sufficient amount to depress the motor cortex with resultant amelioration of abnormal convulsive conditions.

In order that those skilled in the art may be better able to practice the invention, the following examples are given by way of illustration and not by way of limitation.

EXAMPLE 1

This example illustrates the preparation of the dimethyl ester of 3-aminophenylphosphonic acid.

To 6 gms. of dimethyl-3-nitrophosphonate dissolved in 50 ml. of methanol and placed in a Parr hydrogenation bottle was added 0.6 gms. of 10% Pd/C under $N_2$. The mixture was shaken under 50–60 lbs. pressure of $H_2$ until about 50 lbs. of gas were absorbed, filtered and the filtrate evaporated under reduced pressure. The residue was purified by column chromatography using 5% methanol in $CHCl_3$. The product had a melting point of 77°–78° C. and was identified by NMR, IR and C, H, N analyses. IR(KBr): 3320, 3420 ($NH_2$), 1600 (C=C), 1240 (C=O), cm$^{-1}$; NM R($CDCl_3$): 3.55 (s, 3H, $CH_3$), 3.75 (s, 3H, $CH_3$), 4.10 (d, 2H, $NH_2$), 6.60–7.35 (m, 4H, arom.) δ. Anal. Calc. for $C_8H_{12}NO_3P$: C, 47.74; H, 6.02; N, 6.96. Found C, 47.80; H, 6.07; N, 6.91.

EXAMPLE 2

This example illustrates the preparation of the diisopropyl ester of 3-aminophenylphosphonic acid.

To 6 gms of diisopropyl-3-nitrophenylphosphonate dissolved in 50 ml. of isopropanol and placed in a Parr hydrogenation bottle was added 0.6 gms of 10% Pd/C under $N_2$. The mixture was shaken under 50–60 lbs. pressure of $H_2$ until about 50 lbs. of gas were absorbed, filtered and the filtrate evaporated under reduced pressure. The residue was purified by recrystallization from ether-methylene chloride. The product had a m.p. of 104°–105° C. and was identified by NMR, IR and C, H, N analyses. IR(KBr): 3340, 3460 ($NH_2$), 1600 (C=C), 1250 (P=O) cm$^{-1}$; NMR($CDCl_3$): 1.22, 1.35 (2d, 6H, 2$CH_3$), 4.01 (bs, 2H, $NH_2$), 4.65 (m, 2H, 2CH), 6.84–7.25 (m, 4H, arom.)δ. Anal. Calc. for $C_{12}H_{20}NO_3P$: C, 55.99; H, 7.84; N, 5.44. Found C, 56.03; H, 7.88; N, 5.42.

EXAMPLE 3

This example illustrates the preparation of the ethyl ester of o-acetamidophenylphosphate.

To 7.55 g of o-hydroxyacetanilide and 5.56 g of triethylamine in 200 ml. of methylene chloride was added 50 mmole of diethylphosphorochloridate in 50 ml. of methylene chloride at 0°–10° C. with stirring. The reaction mixture was refluxed for 16–18 hours, filtered and the filtrate evaporated under reduced pressure to yield a residue. The residue was chromatographed with 5% methanol in methylene chloride and the fractions containing the product were evaporated to give a liquid which was distilled at 156°–157° C./0.1 mm to yield the pure product. The product was identified by NMR, IR and CHN analyses. IR(neat): 3280(NH), 1690 (C=O), 1610 (C=C), 1275 (P=O) cm$^{-1}$; NMR (CDCl$_3$): 1.33 (t, 6H, 2CH$_3$), 2.20(s, 3H, CH$_3$CO), 4.23 (m, 4H, 2CH$_2$), 7.13 (m, 4H, arom.), 8120 (d, 1H, NH) δ. Anal. Calc. for C$_{12}$H$_{18}$NO$_3$P: C, 50.15; H, 6.32; N, 4.87. Found: C, 50.07; H, 6.35; N, 4.84.

EXAMPLE 4

All tests were performed on male Carworth Farms No. 1 mice by the Antiepileptic Drug Development Program administered by the Section of Epilepsy, National Institutes of Health, Bethesda, MD 20014, according to previously described procedures [DHEW Publication No. (NIH) 76-1093 (1976), Bethesda, MD]. These involved the inhibition of seizures induced by maximal electroshock (MES) and by three subcutaneously administered chemicals: 85 mg/kg pentylenetetrazol (Metrazol) (scMet), 2.7 mg/kg bicuculline (scBic) and 3.2 mg/kg picrotoxin (scPic). Test compounds were solubilized in polyethylene glycol 400 and administered intraperitoneally in a volume of 0.01 ml/g. The time of peak anticonvulsant activity were determined for II (200 mg/kg), III (300 mg/kg) and IV (300 mg/kg) against MES and for I (200 mg/kg) against scMet with dosing of I-III at 0.5, 1.2 and 4 hrs. and I at 0.5, 1 and 2 hrs. using four mice per dose. Neurotoxicity was evaluated by placing an animal on a 1 in. diameter knurled plastic rod and rotating at 6 rpm. Failure of the animal to remain on the rod for 1 min. signified neurological toxicity. This testing was performed using groups of eight mice on a time course basis by dosing with I (900 mg/kg), II (400 mg/kg) and III (360 mg/kg) after 0.5, 1, 2 and 4 hrs. and with IV (580 mg/kg) after an additional 6 and 24 hrs. The neurotoxicity was also similarly quantified, with observations taken 30 mins. after dosing, as follows (compound/mg/kg): I, 400, 500, 600, 700, 800, 900; II, 350, 400, 430, 470; III, 230, 260, 300, 360, 420; IV, 150, 300, 400, 500, 580, 600. Quantification of anticonvulsant activity was similarly determined as follows (compound, test, mg/kg), I, MES, 100, 140, 150, 160, 170, 190, 250; I, scMet, 140, 200, 240, 300, 400, 500; I, scBic, 350, 400, 450, 475, 500; I, scPic, 150, 250, 330, 440, 500; II, MES, 130, 170, 200, 230; II, scMet, 150, 180, 230, 300; III, MES, 220, 240, 280, 290, 300; III, scMet, 300, 400, 500, 600; IV, MES, 150, 220, 300, 400, 500, 600; IV, scMet, 300, 410, 470, 600, 760. From this data the ED$_{50}$ and TD$_{50}$ values and their confidence limits were calculated [Litchfield and Milcoxon, 1947].
I = dimethyl ester of 3-aminophenylphosphonic acid;
II = diethyl ester of 3-aminophenylphosphonic acid;
III = diisopropyl ester of 3-aminophenylphosphonic acid; and IV = diethyl-2-acetamidophenylphosphate.

Figure 2:
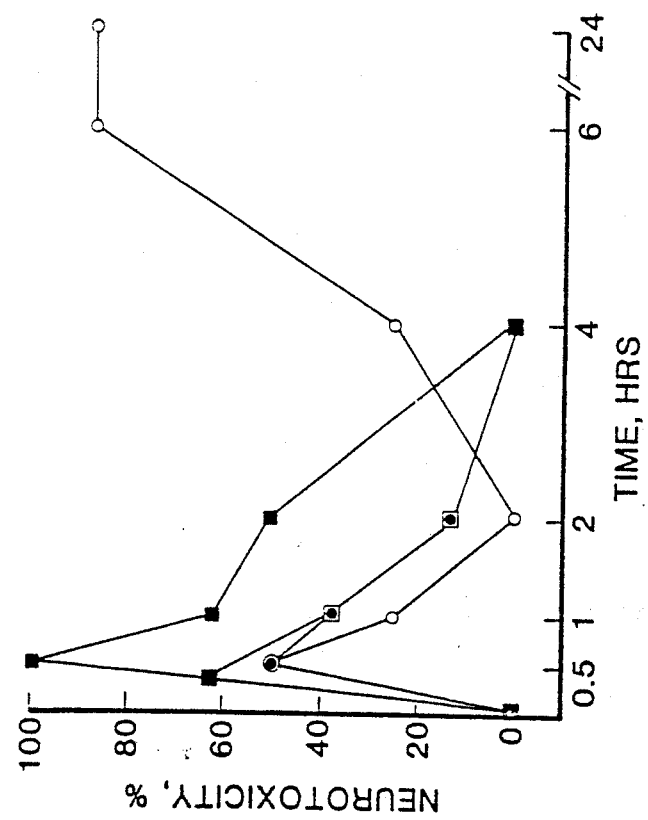
FIG. 2 is also a graphical illustration showing the time course of neurotoxicity produced by intraperitoneally administered I-IV. Key: (■) I (dimethyl ester of 3-aminophenylphosphonic acid) 900 mg/kg; (●) II (diethyl ester of 3-aminophenylphosphonic acid) 400 mg/kg; (□) III (diisopropyl ester of 3-aminophenylphosphonic acid) 360 mg/kg; (○) IV (diethyl-2-acetamidophenylphosphate) 580 mg/kg.

The effect of intraperitoneally administered doses of I-IV over a two (I) or four (II-IV) hour period against convulsions induced in mice by MES and scMet are shown in FIG. 1. Each compound reached its peak effect after 30 minutes compared to such times reported for valproic acid (VPA) (16 minutes), ethosuximide (30 minutes), phenobarbital (60 minutes), and trimethadione (60 minutes) [Kupferberg, 1980]. Compound IV displayed a slight degree of latent protective effect. This might be attributed to some metabolic transformation product such as that obtained by removal of the acetyl group from the acetamido moiety. A delayed neurotoxicity was also noted with this compound (q.v.). The time course of neurotoxic effects were also similarly recorded over a four (I-III) or 24 (IV) hour time period (FIG. 2). Neurotoxicity peaked after 30 minutes in the case of I-III and, with the exclusion of differing doses, their neurotoxic and anticonvulsant profiles were nearly parallel. Compound IV showed a high and prolonged toxicity beginning after two hours and persisting at this level from 6 to 24 hours. This, again, is indicative of possible metabolic changes and/or delayed distribution of compound or its metabolite(s).

The protection indices, calculated from ED$_{50}$ and TD$_{50}$ values, for inhibition of seizures induced by MES (I-IV) and scMet (I, II and IV) are shown in Table I and compared with those reported for VPA. Compound I was further screened using subcutaneous bicuculline (scBic) and subcutaneous pictroxin (scPic) and the results compared to those reported for VPA, ethosuximide, trimethadione and phenobarbital [Kupferberg, in "Antiepileptic Drugs, Mechanisms of Action, Advances in Neurology", G. H. Glaser, J. K. Penry and D. M. Woodbury, Eds., Raven Press, New York, 1980, pp. 643-654].

TABLE 1

Anticonvulsant Activity of Valproic Acid (VPA)[a] and I-IV.

| Compound | Neurotoxicity test Rotorod TD$_{50}$ (mg/kg) | Anticonvulsant tests MES ED$_{50}$ (mg/kg) | P.I.[b] | scMet ED$_{50}$ (mg/kg) | P.I. |
|---|---|---|---|---|---|
| I | 679.99 (611.85-748.89)[c] | 166.46 (152.24-180.76) | 4.08 | 239.93 (195.60-283.69) | 2.83 |
| II | 389.25 (362.98-405.56) | 175.43 (138.19-209.20) | 2.22 | 208.73 (169.76-259.17) | 1.86 |
| III | 311.32 (279.34-349.59) | 266.49 (250.11-278.00) | 1.17 | — | — |
| IV | 458.09 (391.98-509.88) | 348.43 (287.12-410.83) | 1.31 | 444.14 (368.40-515.68) | 1.03 |
| VPA | 425.84 (368.91-450.40) | 217.66 (246.97-337.89) | 1.57 | 148.59 (122.64-177.02) | 2.87 |

[a]Data taken from Kupferberg, 1980.
[b]P.I. = protective index (TD$_{50}$/ED$_{50}$).
[c]95% confidence interval.

TABLE II

Anticonvulsant Activity of Valproic Acid, Ethosuximide, Trimethadione, Phenobarbital[a] and I Against Seizures Induced by Subcutaneous Pentylenetetrazol (scMet), Bicuculline (scBic) and Picotoxin (scPic).

| Compound | TD$_{50}$ (mg/kg) | ED$_{50}$ (mg/kg) | | | | | |
|---|---|---|---|---|---|---|---|
| | | scMet (85 mg/kg) | P.I. | scBic (2.7 mg/kg) | P.I.[b] | scPic (3.2 mg/kg) | P.I. |
| I | 679.99 (611.85–748.89)[c] | 239.93 (195.60–180.76) | 2.83 | 435.94 (398.37–465.11) | 1.56 | 336.20 (246.22–478.63) | 2.02 |
| Valproic Acid | 425.84 (368.91–450.40) | 148.59 (122.64–177.02) | 2.87 | 359.95 (294.07–438.54) | 1.18 | 387.21 (341.37–444.30) | 1.10 |
| Ethosuximide | 440.53 (383.09–485.34) | 130.35 (110.99–150.45) | 3.38 | 459.01 (349.92–635.13) | 0.96 | 242.69 (227.84–255.22) | 1.82 |
| Trimethadione | 819.07 (651.77–1095.63) | 300.45 (265.35–325.18) | 2.73 | 532.12 (488.71–571.93) | 1.54 | 408.09 (342.28–488.19) | 2.01 |
| Phenobarbital | 69.01 (62.84–72.89) | 13.17 (5.87–15.93) | 5.24 | 37.72 (26.49–47.39) | 1.83 | 27.51 (20.88–34.82) | 2.51 |

[a]Data taken from Kupferberg, 1980.
[b]P.I., protective index (TD$_{50}$/ED$_{50}$).
[c]95% confidence interval.

This data show that the organophosphorus agents of this invention are effective in the treatment of convulsive disorders. Compound I and II afford greater protection against MES than VPA by factors of 2.6 and 1.4, respectively. While compound I gave nearly identical results as VPA in the scMet test, it was 1.8 and 1.3 times more effective against scPic and scBic, respectively. Its activity profile in all three testing procedures was very similar to trimethadione.

Obviously, other modifications and variations of the present invention are possible in light of the above teachings. It is therefore to be understood that changes may be made in the particular embodiments of this invention which are within the full intended scope of the invention as defined by the appended claims.

I claim:

1. A process for treating a convulsive disorder, said process comprising administering to a host an anticonvulsant effective amount of an organophosphorus compound having the general formula:

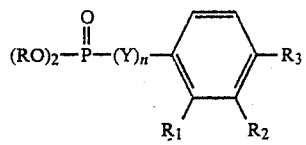

wherein R is alkyl, X is O or S, Y is O or S, n is an integer from 0 to 1, R$_1$, R$_2$ and R$_3$ are selected from the group consisting of NH$_2$ and

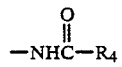

wherein R$_4$ is alkyl, with the proviso that only one of R$_1$, R$_2$ and R$_3$ can be NH$_2$ or

and with the further proviso that when n is 1, R$_1$ or R$_2$ or R$_3$ is

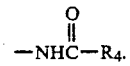

2. The process according to claim 1 wherein said convulsive disorder is epilepsy, parkinsonism, cerebral palsy and Huntington's chorea.

3. The process according to claim 1 wherein said organophosphorus compound has the general formula:

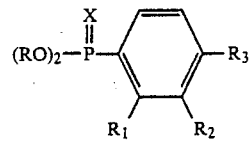

wherein R is alkyl, X is O or S and one of R$_1$, R$_2$ or R$_3$ is NH$_2$.

4. The process according to claim 3 wherein X is O.

5. The process according to claim 3 wherein R$_2$ is NH$_2$ and R$_1$ and R$_3$ are each hydrogen.

6. The process according to claim 3 wherein R$_2$ is NH$_2$, R$_1$ and R$_2$ are each hydrogen and R is selected from the group consisting of methyl and isopropyl.

7. The process according to claim 3 wherein R$_2$ is NH$_2$, R$_1$ and R$_3$ are each hydrogen and R is methyl.

8. The process according to claim 1 wherein said organophosphorus compound has the general formula:

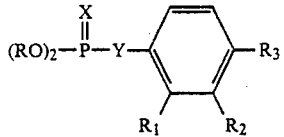

wherein R is alkyl, X is O or S, Y is O or S, and wherein one of R$_1$, R$_2$ or R$_3$ is

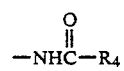

wherein R$_4$ is alkyl.

9. A pharmaceutical composition in dosage unit form which is useful in treating convulsive disorders comprising from about 2 mg to about 300 mg of an organophosphorus compound having the general structure:

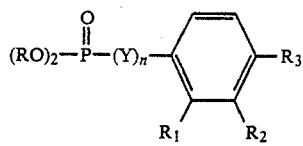

wherein R is alkyl, X is O or S, Y is O or S, n is an integer from 0 to 1, $R_1$, $R_2$ and $R_3$ are selected from the group consisting of $NH_2$ and

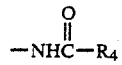

wherein $R_4$ is alkyl, with the proviso that only one of $R_1$, $R_2$ and $R_3$ can be $NH_2$ or

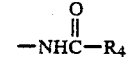

and with the further proviso that when n is 1, $R_1$ or $R_2$ or $R_3$ is

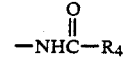

and a pharmaceutically acceptable carrier.

10. The pharmaceutical composition of claim 9 wherein said organophosphorus compound is selected from the group consisting of dimethyl ester of 3-aminophenylphosphonic acid, the diethylester of 3-aminophenylphosphonic acid and the diisopropyl ester of 3-aminophenylphosphonic acid.

11. The pharmaceutical composition of claim 9 wherein said organophosphorus compound is diethyl-2-acetamidophenylphosphate.

* * * * *